United States Patent [19]
Aceti et al.

[11] Patent Number: 5,881,159
[45] Date of Patent: Mar. 9, 1999

[54] DISPOSABLE HEARING AID

[75] Inventors: John G. Aceti, Cranbury; Marvin A. Leedom, Princeton, both of N.J.; Walter P. Sjursen, Washington Crossing, Pa.

[73] Assignee: Sarnoff Corporation, Princeton, N.J.

[21] Appl. No.: 815,852

[22] Filed: Mar. 12, 1997

Related U.S. Application Data

[60] Provisional application No. 60/006,431, filed Mar. 14, 1996.

[51] Int. Cl.⁶ ............................................... H04R 25/00
[52] U.S. Cl. ........................... 381/328; 381/324; 381/322
[58] Field of Search .......................... 381/68, 68.2, 68.3, 381/68.4, 68.5, 68.6, 68.7, 69, 69.2, 312, 314, 322, 323, 328, 327, 60, 324; 181/129, 130, 135; 29/834, 841

[56] References Cited

U.S. PATENT DOCUMENTS

| | | |
|---|---|---|
| 3,527,901 | 9/1970 | Geib . |
| 3,598,928 | 8/1971 | Hickox .................................... 381/68.6 |
| 3,783,201 | 1/1974 | Weiss et al. ............................ 179/107 |
| 4,539,440 | 9/1985 | Sciarra ................................... 381/68.6 |
| 4,639,556 | 1/1987 | Hartl et al. ............................. 381/68.6 |
| 4,712,245 | 12/1987 | Lyregaard ............................. 381/68.6 |
| 4,716,985 | 1/1988 | Haertl ..................................... 181/130 |
| 4,870,688 | 9/1989 | Voroba et al. ............................. 381/60 |
| 4,969,534 | 11/1990 | Kolpe et al. ............................ 181/130 |
| 5,002,151 | 3/1991 | Oliveira et al. ......................... 181/130 |
| 5,012,520 | 4/1991 | Steeger ..................................... 381/68 |
| 5,141,455 | 8/1992 | Ponn ....................................... 439/620 |
| 5,146,051 | 9/1992 | Hermann ................................ 181/130 |
| 5,185,802 | 2/1993 | Stanton ................................. 381/68.6 |

*Primary Examiner*—Huyen Le
*Attorney, Agent, or Firm*—William J. Burke

[57] ABSTRACT

A hearing aid includes an electronic assembly mounted in a cylindrical shell with the shell being mounted in an opening in a ear mold. The electronics assembly includes a printed circuit strip having thereon a speaker, a microphone and electronic components forming a signal processing circuit for amplifying the sound. The ear mold is of a soft, durable and compliant material so that it will fit tightly in the ear of a user. The hearing aid is of optimum design having a minimum number of components and is easy to assemble on an automatic basis. This provides a hearing aid which is relatively inexpensive so as to be disposable.

10 Claims, 2 Drawing Sheets

DISPOSABLE HEARING AID

This non-provisional U.S. national application, filed under 35 U.S.C. 111(a) claims, under 35 U.S.C 119(e)(1), the benefit of the filing date of provisional U.S. application Ser. No. 60/006,431, filed under 35 U.S.C. 111(b) on Mar. 14, 1996.

FIELD OF THE INVENTION

The present invention is directed to a disposable hearing aid, and, more particularly to a hearing aid that is small and very inexpensive so as to be disposable.

BACKGROUND OF THE INVENTION

Modern hearing aids comprise an ear mold having therein the necessary electronic for amplifying sound. Such electronics generally include a microphone for receiving the sound and converting the sound to an electrical signal, an electronic circuit for processing the signal produced by the microphone, a speaker for emitting the amplified sound and a battery for operating the system. The ear mold is generally made of a hard plastic which is specially designed and molded to fill the ear of the party who is to use the hearing aid. The ear mold is made of a hard plastic so as to have a long life and so that it can be periodically cleaned. The electronics of the signal processing circuitry are generally adjusted to meet the specific hearing requirements of the party who is to use the hearing aid. These requirements are obtained by first testing the hearing of the party who is to use the hearing aid. After the desired circuit is determined from the tests, the circuit must be finally adjusted by a hearing aid specialist to meet the final requirements of the party. All of the above features of the structure of the hearing aid and the method of making and adjusting it make the hearing aid relatively expensive. Also, the battery in the hearing aid must be replaced periodically since it is small and has only a limited life time of operation. In addition, the hearing aid must be removed from the ear periodically to allow it to be cleaned of ear wax and other contaminates. This not only adds to the cost of operating the hearing aid, but, since most hearing aids are used by elderly persons, it can be difficult for the person to replace the small battery in the small hearing aid. Therefore, it would be desirable to have a hearing aid which is inexpensive with regard to both the structure of the parts of the hearing aid and its method of making, and which can be easily used by the person, particularly the elderly.

SUMMARY OF THE INVENTION

The present invention is directed to a hearing aid which includes a circuit for receiving and amplifying the sound, and a shell surrounding the circuit. An ear mold of a soft, pliable material surrounds the shell and is adapted to fit into and mold to the ear of a person.

The present invention is also directed to a method of making hearing aids wherein electronic components, speakers, microphones and batteries are mounted onto an elongated flexible circuit strip to form along the strip the electronics assembly of a plurality of hearing aid. The flexible printed circuit strip is cut apart to form the assemblies of individual electronics of a hearing aid on a printed circuit, and each assembly is inserted into a cylindrical shell. Each shell containing an assembly is then inserted into an opening in a separate ear mold of a soft, durable and compliant material.

DETAILED DESCRIPTION

Figure 1:
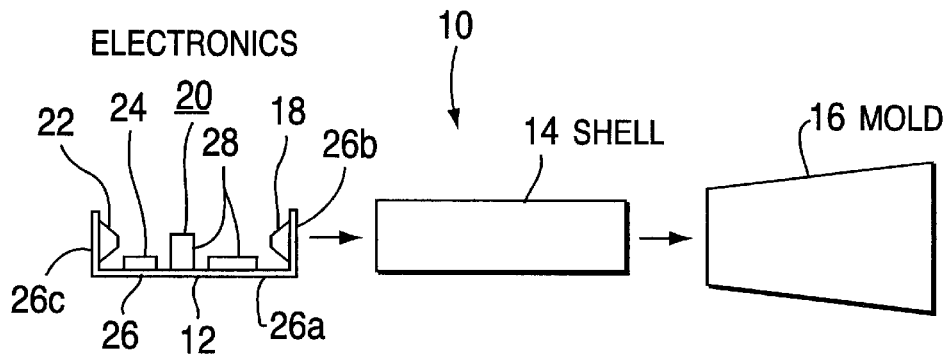
FIG. 1 is an exploded schematic view of the hearing aid of the present invention.
Figure 2:
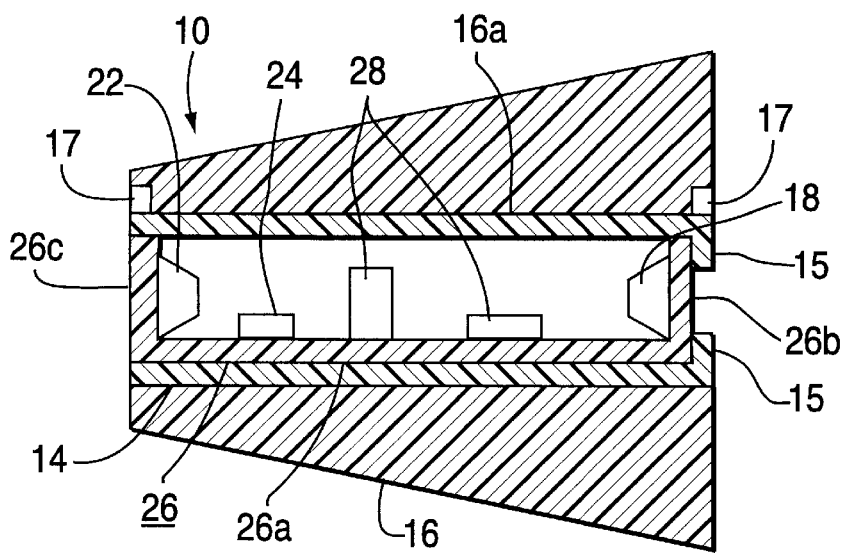
FIG. 2 is a sectional view of the assembled hearing aid of the present invention.
Figure 3:
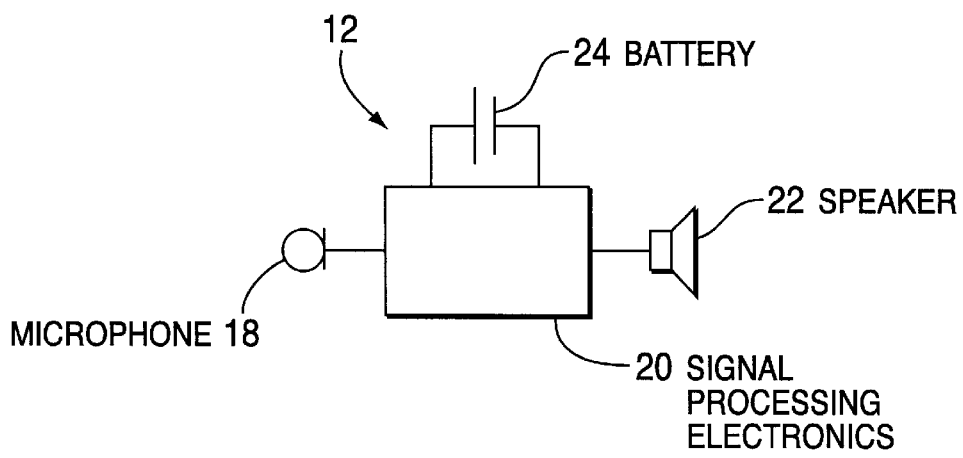
FIG. 3 is a schematic view of the electronics of the hearing aid of the present invention.

Referring initially to FIGS. 1 and 2 of the drawings, the hearing aid of the present invention is generally designated as 10. Hearing aid 10 comprises an electronic assembly 12, a shell 14 and an ear mold 16. As shown in FIG. 3, the electronic assembly 12 includes a microphone 18 which is adapted to receive the sound and convert the sound into electrical signals. The microphone 18 is connected to the input of a signal processing circuitry 20 which amplifies the sound, diminishes any undesirable back ground noise and which can adjust the sound according to the particular needs of the hearing of the user. The output of the signal processing circuitry is connected to a speaker 22 which converts the output signals to sound and directs the sound into the ear of the user. A suitable battery 24 of any desired structure is connected to the signal processing circuitry 20 to operate the circuitry 20.

As shown in FIGS. 1 and 2, the electronics 12 includes a flexible printed circuit 26 having a base 26a and upright arms 26b and 26c at its ends. The flexible printed circuit 26 also includes therein paths of a conductive metal (not shown). The microphone 18 is mounted on the upright arm 26b at one end of the printed circuit 26, and the speaker 22 is mounted on the upright arm 26c at the other end of the printed circuit 26. The components 28 of the signal processing circuitry 20 and the battery 24 are mounted on the base 26a of the printed circuit 26 between its ends. The microphone 18 can be any very small microphone which is presently on the market or can be a silicon microphone in which the diaphragm of the microphone 18 is a thin layer of silicon.

The signal processing circuitry 20 can be of any well known type which will provide the desired amplification. For a very short operating hearing aid 10, such as for a three day operation, the signal processing circuitry 20 can be of the type which will provide amplification with fixed gain and frequency response. A simple, low-cost class-A amplifier can be used. For a longer lasting hearing aid 10, such as a 30 day device, the signal processing circuitry 20 can be of the type which contains a two-channel amplifier with signal compression. One channel can process the lower frequency spectrum while the other channel can process the higher frequency spectrum. To extend battery life, a more efficient class-D amplifier can be used. For any type of signal processing circuitry 20, integrated circuits that perform the required signal processing should be used and are readily available. To achieve the different responses, different values of passive components, such as resistors and capacitors, can be used. The speaker 22 can be of any type of small speaker readily available. The battery 24 can be of any small type having sufficient power to operate the signal processing circuitry used.

The shell 14 is a flexible hollow cylindrical element that is adapted to house and protect the electronics 12. The shell 14 is of a molded, flexible plastic material and contains means, such as ribs 15 shown in FIG. 2, to orient and retain the electronics 12 therein. The shell 14 is of a material which protects the electronics 12 from moisture and mechanical damage. The shell 14 also provides acoustical features for facilitating incoming and outgoing sound, and has external features, such as ribs 17, which help retain it in the earplug 16.

Ear mold 16 is of a soft, durable and compliant material. It can be of a cold-cured methacrylate, heat-cured methacrylate, heat-cured silicone, polyvinyl chloride copolymer or polyethylene co-polymer. The ear. mold 16 has an inner opening 16a into which the shell 14 containing the electronics 12 is inserted and retained. The outer configuration of the ear mold 16, such as its shape and size, is such that it can be readily inserted in the ear channel of the user and which will flexibly mold itself to the shape of the ear channel. Since the ear mold 16 is of a compliant material, the pressure of the ear mold 16 against the wall of the ear channel produces a good fit needed to prevent feedback and to help retain the hearing aid 10 in the ear. It has been found that ear molds of soft material are superior to those of hard material in the attenuation of feed back acoustics.

Figure 4:
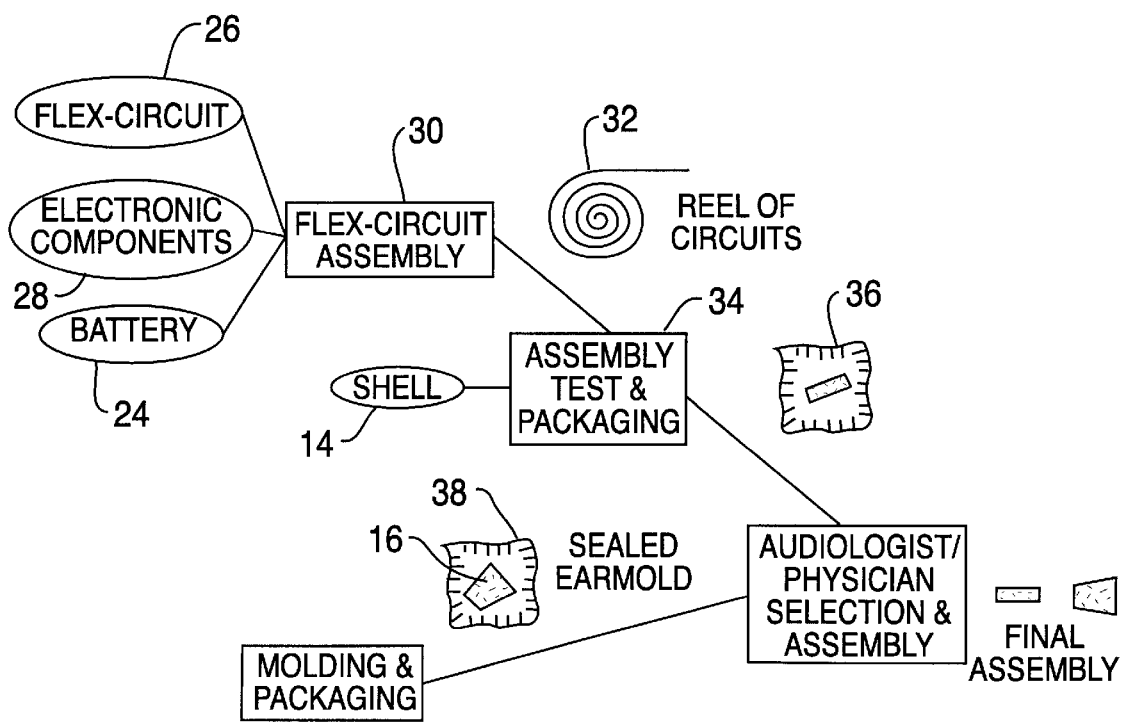
FIG. 4 is a flow chart showing a method of assembling the hearing aid of the present invention.

Referring to FIG. 4, there is illustrated a method of assembling the hearing aid 10 of the present invention. A flexible circuit 26 is feed from a reel along with the various components 28 which made up the electronics 12. Including microphones 18, loudspeakers 22 and batteries 24, into an assembly apparatus 30. The assembly apparatus 30 assembles the components onto the flexible circuit to form a strip containing a plurality of the electronics. 12. The completed assembly is mounted on a reel to form a reel 32 of the circuits.

The flexible circuit assemblies of the reel 32 are then fed along with shells 14 into an assembler 34 where the electronics 12 are cut apart from the reel, and each electronics 12 is formed and inserted into a shell 14. The shell assembly is then inserted into a package 36 which is hermetically sealed and contains a gas which will protect the shell assembly from the atmosphere and extinguish battery activity.

The ear molds 16 are molded in a suitable molding apparatus and packaged in a hermetically sealed package 38. The ear molds 16 are preferably molded in several different sizes so that a suitable size can be used for each user of the hearing aid 10.

Figure 5A:
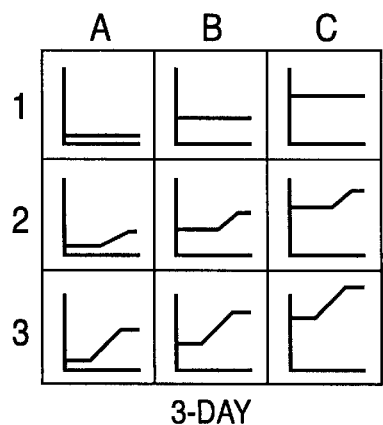
FIGS. 5a and 5b are charts showing the various responses of the amplifier circuit which can be used in the hearing aid of the present invention.
Figure 5B:
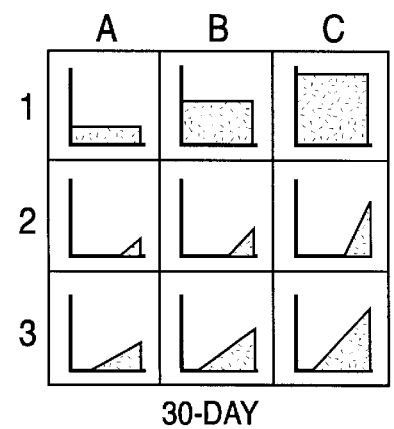

The signal processing circuitry 20 of the electronics 12 is designed to accommodate high-frequency hearing losses and flat-frequency hearing losses in the mild to moderate ranges. The signal processing circuitry 20 for different electronics 12 is made to provide different audiological responses. FIGS. 5a and 5b are charts showing the various responses which are provided by the different electronics 12 which are made in the process of the present invention. FIG. 5a shows the responses for a three day device which has a fixed gain and frequency response, and FIG. 5b shows the responses for a 30 day device which has a two-channel amplifier. In each of FIGS. 5a and 5b, the columns represent different amplifier gains with column A being the lowest gain and column C being the highest gain. The rows represent different frequency responses with row 1 being a flat response, row 2 a mild high frequency boost and row 3 the moderate high frequency boost. Thus, in making the signal processing circuitry 20, different components are used so as to make up a fixed number of circuits having different gains and frequency responses as shown in FIGS. 5a and 5b. The different circuits are marked according to the charts of FIGS. 5a and 5b according to gain and frequency response, such as A1, A2, A3, B1, etc.

The last step in making the hearing aid 10 of the present invention is done by an audiologist or physician after the hearing of the user is tested and it is determined what type of audiological response is required. The audiologist or physician checks the charts shown in FIGS. 5a and 5b and picks the signal processing circuitry 20 which will provide the audiological response required by the user. The audiologist/physician then picks the shell assembly which contains the desired electronics, and picks an ear mold 16 of the appropriate size for the user. The shell assembly is then inserted into the ear mold 16 and the hearing aid 10 is ready to be inserted in the ear of the user.

In the hearing aid 10 of the present invention, the signal processing circuitry 20 has fixed audio characteristics and is made in a limited number of acoustical formats. Also, the acoustical format is preprogrammed in the electronics manufacture so that no potentiometers are needed for adjusting the circuit. In addition, the units are used only for the life of the battery. Thus, no on/off switch is used. Therefore, it is of simple design having a minimum number of components and is easy to assemble on an automatic basis. The signal processing circuitry 20 and the entire electronics 12 is inexpensive because it can be easily made in large volumes and economy of scale. The electronics 12 is encased in a simple hollow shell which is easy to assemble. Also, the ear mold 16 is of simple design and of a soft, pliable material so as to be inexpensive. Thus, the entire hearing aid 10 is of a minimum number of inexpensive parts and is easy to assemble so that the hearing aid 10 is relatively inexpensive compared with presently used hearing aids. Since the hearing aid 10 is so inexpensive it is disposable. Therefore, when the battery 24 of the hearing aid 10 dies out, instead of replacing the battery 24, the whole hearing aid can be disposed of and replaced with a completely new hearing aid 10. Thus, there is provided by the present invention, a hearing aid 10 which is inexpensive to manufacture so as to be disposable. However, the hearing aid 10 still has all of the audio characteristics required by the user and has a high reliability. Furthermore, since the hearing aid of the present invention is small and has a soft, pliable ear mold, it is more comfortable to wear. In addition, since it is disposable, it requires no service calls for major cleaning and adjdustment.

What is claimed is:

1. A hearing aid which is adapted to be inserted in the ear of a user comprising:

an electronic printed circuit board;

a battery permanently mounted to the electronic printed circuit board;

signal processing circuitry electrically coupled to the battery and permanently mounted to the electronic printed circuit board for receiving and amplifying sound signals:

a removable and replaceable shell into which the electronic printed circuit board battery and signal processing circuitry are inserted; and an ear mold of a soft pliable material surrounding the shell and adapted to fit into and mold to the ear of a user.

2. The hearing aid of claim 1 wherein the shell is a flexible, hollow cylindrical element.

3. The hearing aid of claim 2 further including:

a microphone, permanently mounted to the electronic printed circuit board and electrically coupled to the signal processing circuitry; and a speaker, permanently mounted to the electronic printed circuit board and electrically coupled to the battery and the signal processing circuitry.

4. The hearing aid of claim 3 in which the printed circuit board is generally rectangular in shape having first and second ends, and the microphone is mounted on the first end of the printed circuit board, the speaker is mounted on the second end of the printed circuit board, and the signal processing circuitry are mounted on the printed circuit board between the speaker and the microphone.

5. The hearing aid of claim 1 wherein the shell includes means on its inside to orient and retain the electronic circuit therein.

6. The hearing aid of claim 1 in which the ear mold is of a soft pliable material selected from the group of cold-cured methacrylate, heat-cured methacrylate, heat-cured silicone, polyvinyl chloride copolymer and polyethylene co-polymer.

7. A hearing aid which is adapted to be inserted in the ear of a user comprising:

an electronic printed circuit board including signal processing circuitry for receiving and amplifying sound signals the printed circuit board having a base and upright arms at each end, wherein a speaker and a microphone are mounted respectively on the upright arms and the signal processing circuitry and a battery are mounted on the base between the upright arms and electrically connected to each other and to the speaker and the microphone;

a flexible, hollow cylindrical shell surrounding the printed circuit board;

an ear mold of a soft pliable material surrounding the shell and adapted to fit into and mold to the ear of a user.

8. The hearing aid of claim 7 in which the signal process circuitry includes an amplifier.

9. The hearing aid of claim 8 in which the amplifier is a low-cost class A amplifier.

10. The hearing aid of claim 8 in which the amplifier is a two-channel amplifier with signal compression.

* * * * *

UNITED STATES PATENT AND TRADEMARK OFFICE
CERTIFICATE OF CORRECTION

| | | |
|---|---|---|
| PATENT NO. | : 5,881,159 | Page 1 of 1 |
| APPLICATION NO. | : 08/815852 | |
| DATED | : March 9, 1999 | |
| INVENTOR(S) | : John G. Aceti, Marvin A. Leedom and Walter P. Sjursen | |

It is certified that error appears in the above-identified patent and that said Letters Patent is hereby corrected as shown below:

Cover Page:

Please replace the Related U. S. Application Data, with the following amended data:

-- [60] Provisional application No. 60/013,426, filed Mar. 14, 1996. --

Column 1, lines 3-7:

Please replace this paragraph with the following amended paragraph:

-- This non-provisional U.S. national application, filed under 35 U.S.C. 111(a) claims, under 35 U.S.C. 119(e)(1), the benefit of the filing date of provisional U.S. application Ser. No. 60/013,426, filed under 35 U.S.C. 111(b) on Mar. 14, 1996. --

Signed and Sealed this

Eighth Day of April, 2008

JON W. DUDAS
*Director of the United States Patent and Trademark Office*